United States Patent
Kumakura et al.

(10) Patent No.: US 11,674,927 B2
(45) Date of Patent: Jun. 13, 2023

(54) EDDY CURRENT FLAW DETECTION APPARATUS

(71) Applicant: Tex Riken Co., Ltd., Nishinomiya (JP)

(72) Inventors: Yuji Kumakura, Nishinomiya (JP); Nobuhiko Konishi, Nishinomiya (JP)

(73) Assignee: Tex Riken Co., Ltd., Nishinomiya (JP)

( * ) Notice: Subject to any disclaimer, the term of this patent is extended or adjusted under 35 U.S.C. 154(b) by 184 days.

(21) Appl. No.: 17/147,576

(22) Filed: Jan. 13, 2021

(65) Prior Publication Data
US 2021/0231613 A1 Jul. 29, 2021

(30) Foreign Application Priority Data
Jan. 28, 2020 (JP) .............................. JP2020-011486

(51) Int. Cl.
*G01N 27/90* (2021.01)
*G01N 33/2045* (2019.01)
*H03F 3/21* (2006.01)

(52) U.S. Cl.
CPC ..... *G01N 27/9046* (2013.01); *G01N 33/2045* (2019.01); *H03F 3/211* (2013.01)

(58) Field of Classification Search
CPC ........... G01N 27/9046; G01N 33/2045; G01N 27/904; H03F 3/211
See application file for complete search history.

(56) References Cited

U.S. PATENT DOCUMENTS

| | | | | |
|---|---|---|---|---|
| 5,146,164 A | * | 9/1992 | Masui | G01N 27/904 324/237 |
| 2015/0323502 A1 | * | 11/2015 | Suetsugu | G01N 27/902 324/240 |
| 2016/0123928 A1 | * | 5/2016 | Kobayashi | G01N 27/9006 324/238 |
| 2016/0356743 A1 | * | 12/2016 | Miki | G01N 27/902 |
| 2021/0215639 A1 | * | 7/2021 | Iijima | G01N 27/82 |

FOREIGN PATENT DOCUMENTS

JP 2882856 B2 4/1999

\* cited by examiner

*Primary Examiner* — Jermele M Hollington
*Assistant Examiner* — Zannatul Ferdous
(74) *Attorney, Agent, or Firm* — Muncy, Geissler, Olds & Lowe, P.C.

(57) ABSTRACT

The eddy current flaw detection apparatus includes: a pair of detecting coils 10a, 10b arranged in coaxial and spaced relation with a specimen 3; and a bridge circuit two sides of which are constituted by the detecting coils so that magnetic fields generated by these detecting coils 10a, 10b are in opposite phases to each other. A pair of exciting coils 11a, 11b are arranged coaxially with the detecting coils 10a, 10b in a manner to sandwich the pair of detecting coils 10a, 10b therebetween. A distance D between the detecting coil and the exciting coil adjacent thereto is set to a distance where a vibrational noise signal excited in the exciting coil and detected by its adjacent detecting coil is in opposite phase to that of a vibrational noise signal excited in the detecting coil and detected by the detecting coil.

12 Claims, 5 Drawing Sheets

EDDY CURRENT FLAW DETECTION APPARATUS

BACKGROUND OF THE INVENTION

Technical Field

The present invention relates to an eddy current flaw detection apparatus. More specifically, the invention relates to an eddy current flaw detection apparatus which includes a coil for generating an eddy current at a surface layer of a specimen, and a signal processing part for processing signal induced by impedance change of the coil, and which inspects the specimen for any flaw and the like on the basis of the signal.

Background Art

For example, patent document 1 discloses an eddy current flaw detection apparatus in which a pair of detecting coils are arranged in contactless and coaxial relation with a conductor as a specimen; a pair of resonance coils are disposed between the pair of detecting coils and in coaxial relation with the detecting coils such that magnetic fields so generated are in phase to each other; and a capacity circuit is disposed at the resonance coils.

CITATION LIST

Patent Document

[Patent Document 1] JP-B2 No. 2882856

SUMMARY OF THE INVENTION

In the eddy current flaw detection apparatus set forth in the patent document 1, in a case where the conductor contains no flaw or foreign matter therein, induction currents flowing through the resonance coils cancel each other out and hence, there occurs no change. On the contrary, in a case where the conductor in the above-described apparatus contains some flaw or foreign matter therein, there occurs some unevenness in the magnetic fields generated by the detecting coils. Therefore, a difference occurs between the values of induction currents generated by the resonance coils and hence, a current equivalent to the difference flows to make the resonance coils resonate. Thus, the above-described apparatus can achieve improved S/N ratio.

According to the above-described patent document 1, however, the eddy current flaw detection apparatus has the following problem. In a case where a noise signal is induced by vibrations of the eddy current flaw detection apparatus or by eccentricity or vibrations of the specimen, the S/N ratio is decreased by the noise signal.

Further, according to the above-described patent document 1, the resonance coils each require an amplification circuit for amplifying an output. This leads to a drawback of increased complexity of the apparatus.

An object of the invention is to provide an eddy current flaw detection apparatus as an inspection apparatus which does not entail the increased complexity of the apparatus but can remove the noise signals induced by the vibrations of the eddy current flaw detection apparatus or induced by the eccentricity or vibrations of the specimen.

According to an aspect of the invention for achieving the above object, an eddy current flaw detection apparatus includes: a pair of detecting coils arranged in contactless and coaxially spaced relation with a specimen; and
a bridge circuit two sides of which are constituted by the detecting coils so that magnetic fields generated by these detecting coils are in opposite phases to each other, and has a configuration wherein
a pair of exciting coils are arranged in a coaxial relation with the detecting coils in a manner to sandwich the detecting coils therebetween, and
a distance between the detecting coil and the exciting coil adjacent thereto is set to a distance where a phase between an eccentricity-induced or vibration-induced noise signal which is excited in the exciting coil and detected by its adjacent detecting coil, and an eccentricity-induced or vibration-induced noise signal which is excited in the detecting coil and detected by the detecting coil changes.

According to another aspect of the invention, it is preferred that the distance between the detecting coil and the exciting coil adjacent thereto is set to a distance where the eccentricity-induced or vibration-induced noise signal which is excited in the exciting coil and detected by its adjacent detecting coil, and the eccentricity-induced or vibration-induced noise signal which is excited in the detecting coil and detected by the detecting coil are in opposite phases to each other.

According to another aspect of the invention, it is preferred that a phase of an AC power to the exciting coil is converted before the AC power is applied to the exciting coil so that the eccentricity-induced or vibration-induced noise signal which is excited in the exciting coil by the application of the AC power and detected by its adjacent detecting coil is in opposite phase to that of the eccentricity-induced or vibration-induced noise signal which is excited in the detecting coil by the application of the AC power and detected by the detecting coil.

According to another aspect of the invention, the specimen is a round bar, and the detecting coil and the exciting coil are encircling coils, and the distance between the detecting coil and the exciting coil adjacent thereto may be set based on a difference between an outside diameter of the round bar and an inside diameter of the detecting coil and the exciting coil.

The invention can provide an eddy current flaw detection apparatus which can remove the noise signals induced by the vibrations of the eddy current flaw detection apparatus or induced by the eccentricity or vibrations of the specimen, thus achieving an improved S/N ratio.

DETAILED DESCRIPTION OF THE INVENTION

Next, the eddy current flaw detection apparatus according to the embodiments of the invention will be specifically described with reference to the accompanying drawings. It is noted that the eddy current flaw detection apparatus according to the invention is not limited to the following embodiments but can be embodied in other specific forms as needed without departing from the spirit or essential characteristics thereof.

Figure 1:
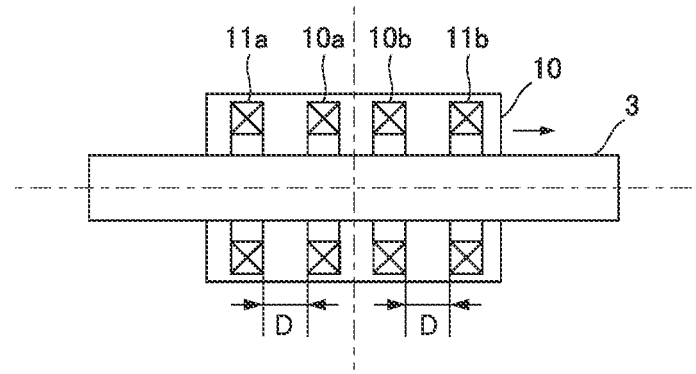
FIG. 1 is a schematic diagram showing an eddy current flaw detection apparatus and a specimen according to the invention.

As shown in FIG. 1, a specimen 3 of the invention is a conductor such as a pipe or a round bar. A probe 10 is disposed in proximity to this specimen 3. This probe 10 is formed in a cylindrical or semicylindrical shape and contains therein a pair of detecting coils 10a, 10b and a pair of exciting coils 11a, 11b sandwiching the detecting coils 10a, 10b therebetween. According to the embodiment, the probe 10 is formed in a cylindrical shape. The pair of detecting coils 10a, 10b and the pair of exciting coils 11a, 11b contained in the probe are constituted by encircling coils.

The detecting coils 10a, 10b and the exciting coils 11a, 11b are arranged in contactless and coaxially spaced relation with the specimen 3. The probe 10 and the specimen 3 are moved relative to each other. Specifically, there is a care where the eddy current flaw detection apparatus inspects the specimen 3 by means of the probe 10 moved relative to the specimen 3; and a case where the specimen 3 moves relative to the fixed probe 10. The eddy current flaw detection apparatus of the embodiment inspects conditions of a surface and the like of the specimen 3 by means of the probe 10 moved relative to the specimen 3 in a direction of the arrow in the figure.

According to the embodiment, the specimen 3 is a round bar made of metal.

In this embodiment, the detecting coil 10a, 10b and its adjacent exciting coil 11a, 11b are spaced apart by a distance D. As shown in FIG. 1, the exciting coil 11a and the detecting coil 10a as well as the exciting coil 11b and the detecting coil 10b are spaced apart by the distance D. The distance D will be described hereinafter.

Figure 2A:
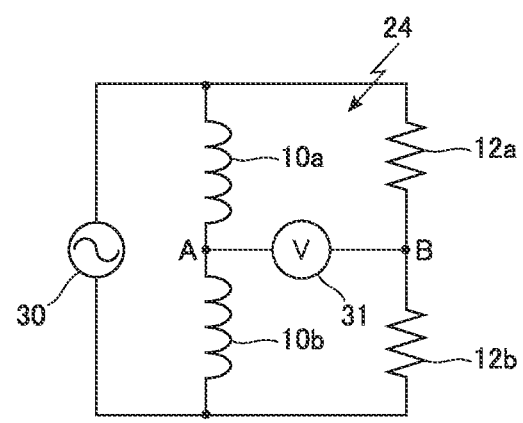
FIG. 2A is a schematic circuit diagram showing a configuration of detecting coils of the eddy current flaw detection apparatus according to the invention.
Figure 2B:
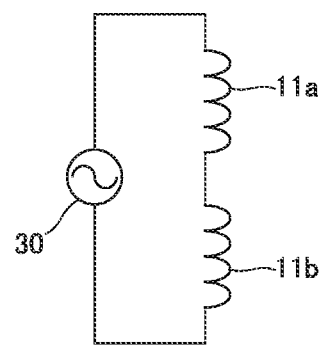
FIG. 2B is a schematic circuit diagram showing a configuration of exciting coils of the eddy current flaw detection apparatus according to the invention.

Next, a brief outline of circuit configurations of the embodiment is given with reference to FIG. 2A and FIG. 2B. FIG. 2A is a schematic circuit diagram showing a configuration of the detecting coils of the eddy current flaw detection apparatus according to the invention. FIG. 2B is a schematic circuit diagram showing a configuration of the exciting coils of the eddy current flaw detection apparatus according to the invention.

As shown in FIG. 2A, a bridge circuit 24 includes: the detecting coils 10a, 10b and resistances 12a, 12b. The detecting coils 10a, 10b are so connected as to define two sides of the bridge circuit 24. The resistances 12a, 12b are so connected as to define the other two sides of the bridge circuit 24.

Figure 3:
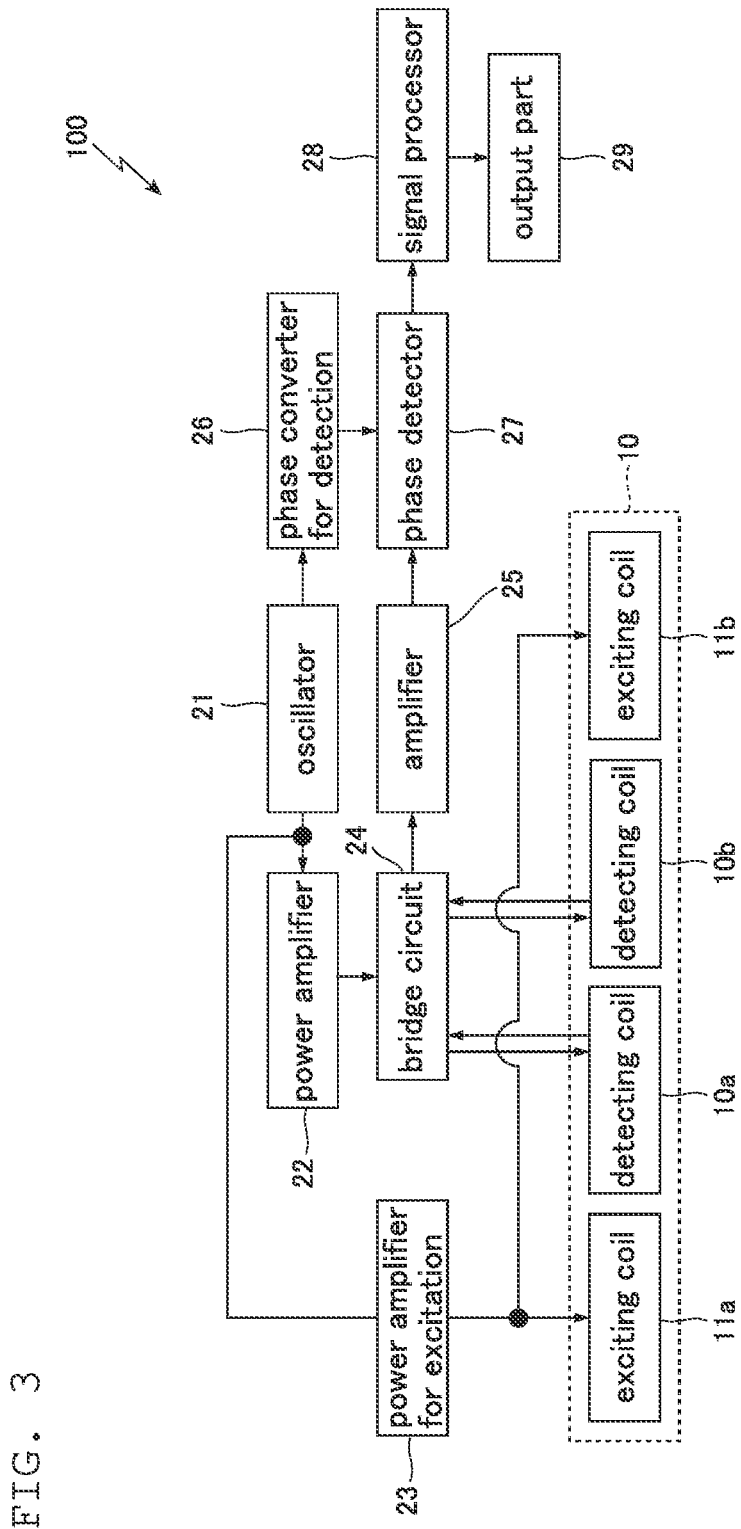
FIG. 3 is a block diagram showing an eddy current flaw detection apparatus according to a first embodiment of the invention.

An AC output from an AC power source 30 (an oscillator 21 and a power amplifier 22 as shown in FIG. 3) is applied to the detecting coils 10a, 10b via the bridge circuit 24, and excites the specimen 3 so that an eddy current is generated. The detecting coils 10a, 10b detect an impedance change associated with change in magnetic flux generated by the eddy current by means of a detector part 31 (a phase detector 27 and the like as shown in FIG. 3).

The detecting coils 10a, 10b are differentially connected such that magnetic fields so generated are in opposite phases to each other. According to the embodiment, the detecting coils 10a, 10b excite the specimen 3 as well as detect the impedance change associated with the change in magnetic flux generated by the eddy current.

As shown in FIG. 2B, the AC output from the AC power source 30 (the oscillator 21 and a power amplifier 23 as shown in FIG. 3) is applied to the exciting coils 11a, 11b so as to excite the exciting coils 11a, 11b. The specimen 3 is excited by the excitation of the exciting coils 11a, 11b so that the eddy current is generated. The exciting coil 11a is wound in a manner that the generated magnetic field is in phase with the detecting coil 10a. The exciting coil 11b is wound in a manner that the generated magnetic field is in phase with the detecting coil 10b.

The detecting coil 10a also detects the impedance change associated with the change in the magnetic flux generated by the eddy current from the specimen 3 excited by the exciting coil 11a.

The detecting coil 10b also detects the impedance change associated with the change in the magnetic flux generated by the eddy current from the specimen 3 excited by the exciting coil 11b.

As just described, the detecting coil 10a detects change in synthetic impedance based on the excitation of its own coil 10a and the excitation of the exciting coil 11a. The detecting coil 10b detects change in synthetic impedance based on the excitation of its own coil 10b and the excitation of the exciting coil 11b. The bridge circuit 24 is conditioned to output a zero-balance signal in a case where the specimen 3 is normal.

An output from between terminals A, B shown in FIG. 2A is outputted by the detector part 31. The specimen 3 can be inspected based on this output signal.

Next, the eddy current flaw detection apparatus according to the first embodiment of the invention is further described with reference to the block diagram of FIG. 3.

As shown in FIG. 3, an eddy current flaw detection apparatus 100 includes the oscillator 21, the power amplifier 22, the power amplifier for excitation 23, the bridge circuit 24, a phase converter for detection 26, an amplifier 25, and the phase detector 27.

The bridge circuit 24 is constituted by the detecting coils 10a, 10b of the probe 10, and the resistances 12a, 12b, as shown in FIG. 2A.

The AC output from the oscillator 21 is amplified by the power amplifier 22 and applied to the detecting coils 10a, 10b via the bridge circuit 24. Further, the AC output from the oscillator 21 is amplified by the power amplifier for excitation 23 and applied to the exciting coils 11a, 11b.

The specimen 3 is excited by the AC output respectively applied to the detecting coil 10a, the exciting coil 11a, the detecting coil 10b and the exciting coil 11b. The detecting coils 10a, 10b detect the impedance change associated with the change in the magnetic flux generated by the eddy current.

An unbalanced output between the detecting coils 10a, 10b, which is outputted from the bridge circuit 24, is amplified by the amplifier 25 and sent to the phase detector 27. The AC output from the oscillator 21 is applied to the phase converter for detection 26. An output from the phase converter for detection 26 is applied to the phase detector 27.

The phase converter for detection 26 converts the signal from the oscillator 21 to a signal in phase with an excitation signal and to a signal 90° out of phase with the excitation signal, and applies the resultant signals to the phase detector 27.

The unbalanced output amplified by the amplifier 25 and the output from the phase converter for detection 26 are applied to the phase detector 27. The outputs from the detecting coils 10a, 10b are demodulated along with the output from the phase converter for detection 26.

The phase detector 27 outputs an X-axis eddy current signal by synchronously demodulating the unbalanced output by means of the signal in phase with the excitation signal, and also outputs a Y-axis eddy current signal by synchronously demodulating the unbalanced output by means of the signal 90° out of phase with the excitation signal. A signal processor 28 acquires the demodulated X-axis eddy current signal and Y-axis eddy current signal via a filter (not shown) and an A/D converter (not shown), and displays the measurement results and the like at an output part 29 such as an indicator. The signal processor 28 consists of, for example, a personal computer (PC) connected to the eddy current flaw detection apparatus 100.

In this embodiment, some flaw and the like of the specimen 3 is detected on the basis of the values outputted from the detecting coils 10a, 10b.

In the above-described eddy current flaw detection apparatus 100, when the vibrations of the probe 10 or the specimen 3 occur or when eccentricity occurs between the probe 10 and the specimen 3, distances between the detecting coils 10a, 10b and the specimen 3 and distances between the exciting coils 11a, 11b and the specimen 3 individually vary so that noise signals are generated.

In the case where the probe 10 moves, the movement of the probe 10 induces the vibrations therein so that the distances between the detecting coils 10a, 10b and the specimen 3 and the distances between the exciting coils 11a, 11b and the specimen 3 individually vary, resulting in the noise signals. In a case where the specimen 3 moves, the movement of the specimen 3 induces the vibrations therein so that the distances between the detecting coils 10a, 10b and the specimen 3 and the distances between the exciting coils 11a, 11b and the specimen 3 individually vary, resulting in the noise signals. Even when there is no vibrations of the probe 10 or the specimen 3, if there is eccentricity between the detecting coil 10a, 10b and the specimen 3 or between the exciting coil 11a, 11b and the specimen 3, the distances between the detecting coils 10a, 10b and the specimen 3 and the distances between the exciting coils 11a, 11b and the specimen 3 individually vary, resulting in the noise signals.

According to this specification, the noise signal induced by eccentricity or vibrations is defined to mean the noise signal caused by the change in the relative distance between the detecting coil 10a, 10b and the specimen 3 due to the vibrations of the coil or the specimen or due to the eccentricity of the coil or the specimen.

It is noted here that the inventors have made an intensive study of relations between the distance D between the detecting coil 10a and the exciting coil 11a and the noise signal, and between the distance D between the detecting coil 10b and the exciting coil 11b and the noise signal. As a result, it is found that there is a distance D where a vibrational noise signal excited in the exciting coil and detected by its adjacent detecting coil and an eccentricity-induced or vibration-induced noise signal excited in the detecting coil and detected by the detecting coil are in opposite phases to each other.

Further, the inventors have made an intensive study of a space between the surface of the specimen 3 and the detecting coils 10a, 10b. As a result, it is found that there are optimum values of the space between the surface of the specimen 3 and the detecting coils 10a, 10b, and the distance D between the detecting coil and its adjacent exciting coil.

The inventors have confirmed the following fact. In a case where the specimen 3 is a round bar made of metal, and the detecting coils 10a, 10b and the exciting coils 11a, 11b are the encircling coils, for example, there is an optimum value of the distance D between the detecting coil and its adjacent exciting coil depending upon a difference between an outside diameter of the round bar and an inside diameter of the coil. Specific examples of the confirmed fact will be described hereinafter.

In the first embodiment of the invention, determined is a distance D between the exciting coil and its adjacent detecting coil where their respective eccentricity-induced or vibration-induced noise signals are in opposite phases. The individual coils are arranged in the probe 10 in a manner that the exciting coil 11a and the detecting coil 10a are spaced apart by the distance D and that the exciting coil 11b and the detecting coil 10b are spaced apart by the distance D. In this manner, the eddy current flaw detection apparatus 100 can remove the eccentricity-induced noise or the vibration-induced noise even in the case where the vibrations of the probe 10 or the eccentricity of the specimen 3 occur in the eddy current flaw detection apparatus 100.

The optimization of the distance D between the exciting coil and the detecting coil provides the vibrational noise signal which is excited in the exciting coil and detected by its adjacent detecting coil and is in opposite phase to that of the vibrational noise signal which is excited in the detection coil and detected by the detection-side coil. That is, the phase of the vibrational noise signal is shifted by 180° against that of the other vibrational signal. As a result, a synthesized signal of the exciting coil and the detecting coil as generated by the eccentricity-induced or vibration-induced noises can be damped.

It is also confirmed that the eddy current generated by the detecting coil and its adjacent exciting coil does not suffer signal change due to a flaw and the like of the specimen 3. As a result, the detection apparatus can remove the noises induced by the eccentricity or vibrations, achieving the improved S/N ratio.

Next, description is made on specific examples of the invention with reference to FIG. 4 to FIG. 7. In the specific examples, the round bar was decentered while the impedance change was detected by the detecting coil. It was confirmed that the noise signals caused by the vibrations or the eccentricity of the specimen can be removed.

Figure 4:
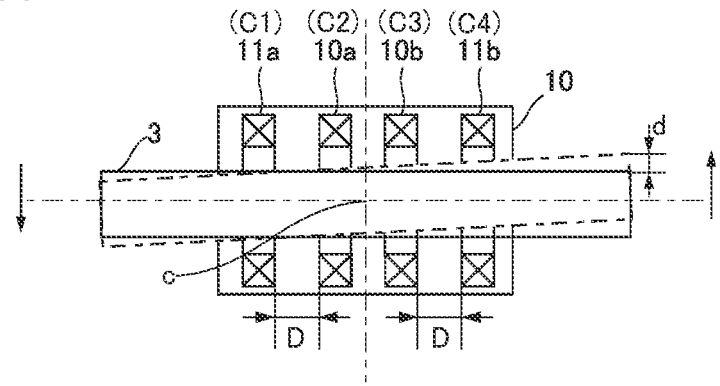
FIG. 4 is a schematic diagram for explaining a specific example where the removal of the noise signal induced by the vibrations of the eddy current flaw detection apparatus according to the invention and induced by the eccentricity or vibrations of the specimen were confirmed.

FIG. 4 is a schematic diagram for explaining a specific example where the removal of the noises induced by the vibrations of the eddy current flaw detection apparatus of the invention, or induced by the eccentricity or vibrations of the specimen was confirmed.

The probe 10 of the specific example shown in FIG. 4 is provided with the detecting coils 10a, 10b and a pair of exciting coils 11a, 11b arranged in a manner to sandwich the detecting coils 10a, 10b therebetween. The detecting coils 10a, 10b and the exciting coils 11a, 11b have the same inside diameter. The specimen 3 constituted by a round bar made of metal is inserted in these coils 10a, 10b, 11a, 11b. A difference between the inside diameter of these coils 10a, 10b, 11a, 11b and the outside diameter of the specimen 3 is 4 mm.

As shown in FIG. 4, the specimen 3 was angularly moved in the direction of the arrows shown in the figure about the center (c) of the length between the detecting coils 10a, 10b and the radial length of the detecting coils. The specimen 3 was stopped when an end of the specimen was moved by a distance d of 2 mm.

An AC power having an excitation frequency of 16 kHZ and a magnetomotive force of 133×10 mA is applied to the detecting coils 10a, 10b and the exciting coils 11a, 11b. The impedance change was detected by the detecting coils 10a, 10b. The application of the AC power to the detecting coils 10a, 10b and the exciting coils 11a, 11b was controllably switched between a case where the AC power is applied only to the detecting coils 10a, 10b and a case where the AC power is applied only to the exciting coils 11a, 11b.

In this specific example, the exciting coil 11a is expressed as Coil C1, the detecting coil 10a expressed as Coil C2, the detecting coil 10b expressed as Coil C3, and the exciting coil 11b expressed as Coil C4.

The probe 10 of the specific example shown in FIG. 4 was used for detecting the impedance change while changing the supply of the AC power to the coils.

First, the AC power was applied only to Coil C1 (exciting coil 11a) and Coil C4 (exciting coil 11b) for excitation. Meanwhile, the impedance change was detected by Coil C2 (detecting coil 10a) and Coil C3 (detecting coil 10b). The detection results are expressed in terms of C1, C4 and are shown in Table 1 and FIG. 5.

In the probe 10 used for confirmation, the distance D between the exciting coil and the detecting coil was varied from 2 mm to 4 mm, 6 mm, 8 mm and 10 mm.

TABLE 1

| C1-C2 SPACE (C3-C4 SPACE) | Vx | Vy |
|---|---|---|
| 2 | −30.9 | 36.0 |
| 4 | −32.3 | 98.3 |
| 6 | −29.9 | 113.4 |
| 8 | −25.7 | 124.8 |
| 10 | −20.2 | 131.3 |

Similarly, the AC power was applied only to Coil C2 (detecting coil 10a) and Coil C3 (detecting coil 10b) for excitation. Meanwhile, the impedance change was detected by Coil C2 (detecting coil 10a) and Coil C3 (detecting coil 10b). The detection results are expressed in terms of C2, C3 and are shown in Table 2 and FIG. 5.

TABLE 2

| C1-C2 SPACE (C3-C4 SPACE) | Vx | Vy |
|---|---|---|
| 2 | 32.0 | −106.4 |
| 4 | 32.0 | −106.4 |
| 6 | 32.0 | −106.4 |
| 8 | 32.0 | −106.4 |
| 10 | 32.0 | −106.4 |

Figure 5:
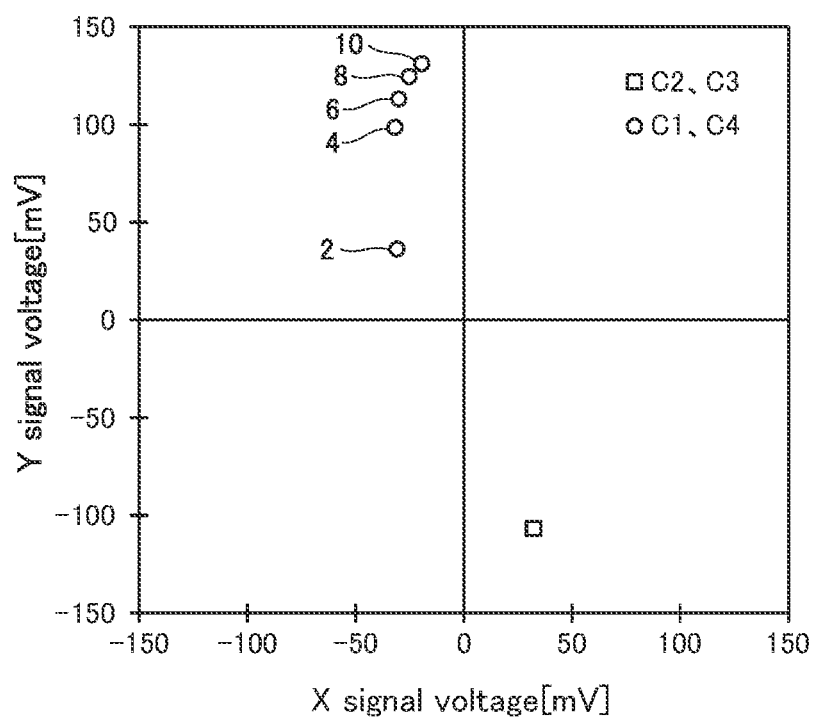
FIG. 5 is a diagram showing a result of measurements of impedance change of the detecting coil when the detecting coil and the exciting coil were each excited independently while changing a distance between the detecting coil and the exciting coil adjacent thereto.

As for Table 1, Table 2 and FIG. 5, the numerical values were calculated as follows. For the impedance change of the detecting coil, an excitation AC frequency is multiplied by a signal having a phase difference of 0° and by a signal having a phase difference of 90°. A phase difference voltage and a voltage magnitude of the detecting coil are calculated so as to be plotted on a two-dimensional surface. In FIG. 5, in-phase components are plotted on the X-axis while quadrature components are plotted on the Y-axis.

In FIG. 5, the circles denote the results of C1 and C4 and the squares denote the results of C2 and C3. Numbers attached to the circles correspond to the distance D between the exciting coil and the detecting coil, respectively.

Table 2 and FIG. 5 indicate that in the case of excitation of only the coil C2 (detecting coil 10a) and the coil C3 (detecting coil 10b), the apparatus takes a constant value even though the specimen 3 is moved. Namely, the detection value is constant even when the specimen 3 is decentered or vibrated.

Further, Table 1 and FIG. 5 indicate that in the case of excitation of only the coil C1 (exciting coil 11a) and the coil C4 (exciting coil 11b), the detection value varies if the distance D between the exciting coil and the detecting coil changes. Namely, when the specimen 3 is decentered or vibrated, the voltage magnitude and the phase vary accordingly.

FIG. 5 indicates that the detection results in the case of excitation of only the coil C2 (detecting coil 10a) and the coil C3 (detecting coil 10b) and the detection results in the case of excitation of only the coil C1 (exciting coil 11a) and the coil C4 (exciting coil 11b) differ in the phase.

Figure 6:
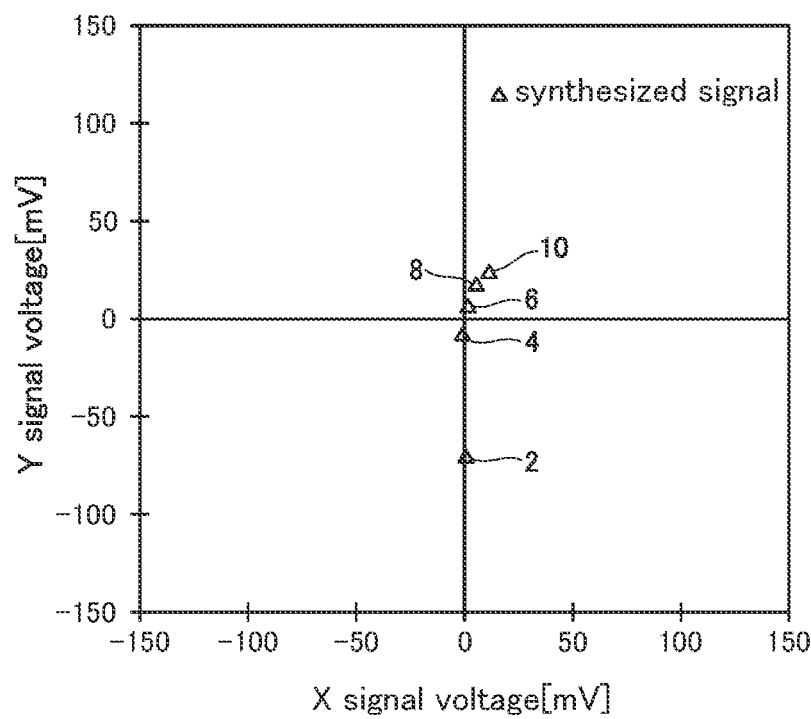
FIG. 6 is an illustrative diagram showing synthesized signals of the detecting coil when the detecting coil and the exciting coil were each excited independently while changing the distance between the detecting coil and the exciting coil adjacent thereto.

Next, calculation results of synthesized signals of the detection values of the excited coil C2 (detecting coil 10a) and the excited coil C3 (detecting coil 10b) and the detection values of the excited coil C1 (exciting coil 11a) and the excited coil C4 (exciting coil 11b) are shown in Table 3 and FIG. 6. The numerical values of Table 3 and FIG. 6 are calculated in the same way as those of the above Table 1, Table 2 and FIG. 5.

TABLE 3

| C1-C2 SPACE (C3-C4 SPACE) | Vx | Vy |
|---|---|---|
| 2 | 1.1 | −70.4 |
| 4 | −0.3 | −8.2 |
| 6 | 2.1 | 7.0 |
| 8 | 6.3 | 18.3 |
| 10 | 11.8 | 24.8 |

Table 3 and FIG. 6 indicate that if the detection value of the excited coil C2 (detecting coil 10a) and the excited coil C3 (detecting coil 10b) is synthesized with the detection value of the excited coil C1 (exciting coil 11a) and the excited coil C4 (exciting coil 11b), the resultant signal approaches a zero point position, indicating that the eccentricity-induced or vibration-induced noises can be reduced. In FIG. 6, the triangles denote the synthesized signals and the numbers attached to the triangles correspond to the distance D between the exciting coil and the detecting coil, respectively.

As shown in FIG. 6, the individual detection signals have different phases and hence, the eccentricity-induced or vibration-induced noises are cancelled out with each other so that the noises can be reduced. The Figure also indicates that there is the distance D between the exciting coil and the detecting coil where the eccentricity-induced noise or vibration-induced noise signal excited in the coil C1 (exciting coil 11a), the coil C4 (exciting coil 11b) and detected by the detecting coils 10a, 10b, and the eccentricity-induced noise or vibration-induced noise signal excited in the coil C2 (detecting coil 10a), the coil C3 (detecting coil 10b) and detected by the detecting coils 10a, 10b are in the opposite phases to each other.

Figure 7:
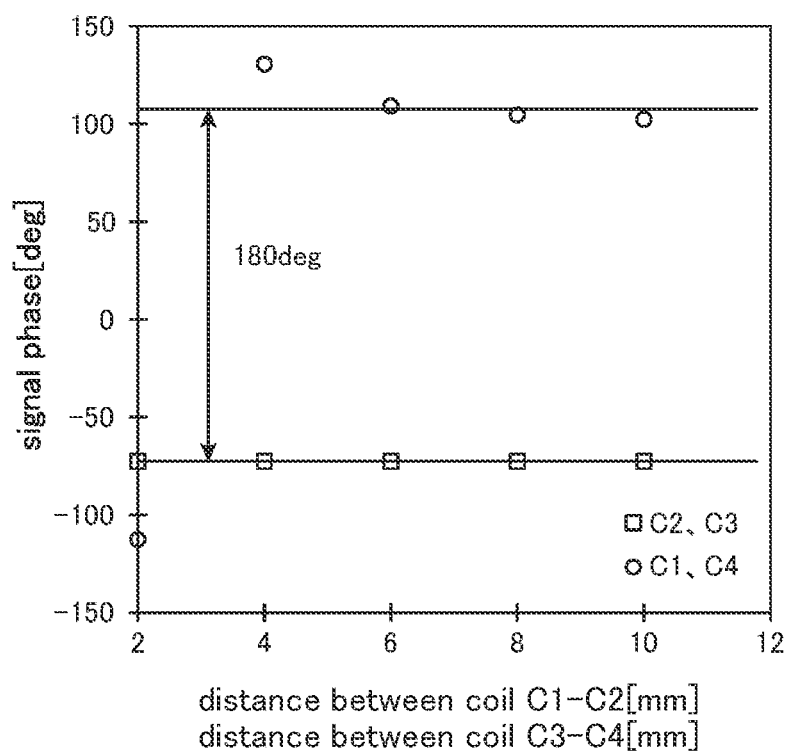
FIG. 7 is an illustrative diagram showing a relation between a distance and a phase when the distance between the detecting coil and the exciting coil adjacent thereto was changed.

In order to confirm the distance D between the exciting coil and the detecting coil where the two detection signals are in opposite phases to each other, the phases of the two detection signals are calculated. The results are shown in Table 4 and FIG. 7. In FIG. 7, C2, C3 denote phase values of the detection values of the excited coil C2 (detecting coil 10a), the excited coil C3 (detecting coil 10b). In the figure, C1, C4 denote phase values of the detection values of the excited coil C1 (exciting coil 11a), the excited coil 4 (exciting coil 11b). In FIG. 7, the circles denote the results of C1, C4, while the squares denote the results of C2, C3.

TABLE 4

| C1-C2 SPACE (C3-C4 SPACE) | C2, C3 PHASE | C1, C4 PHASE |
|---|---|---|
| 2 | −72.62 | −112.79 |
| 4 | −72.62 | 130.57 |
| 6 | −72.62 | 108.21 |
| 8 | −72.62 | 104.75 |
| 10 | −72.62 | 101.64 |

Table 4 and FIG. 7 indicate that when the distance D between the exciting coil and the detecting coil is 6 mm, the two detection signals thereof are in almost opposite phases to each other. That is, a phase difference between the two detection signals is nearly 180°. Therefore, there is a distance where the two detection signals are in opposite to each other when the distance D between the exciting coil and the detecting coil is in vicinity of 6 mm. The noises induced by eccentricity or vibrations can be cancelled out with each other by setting the distance D between the exciting coil and the detecting coil to the distance where the two signals are in opposite phases to each other. Thus, the noises can be removed. It is also confirmed that the eddy current signal induced by a flaw and the like of the specimen 3 does not change.

Consequently, it is confirmed that the invention is adapted to remove the eccentricity-induced or vibration-induced noises by setting the distance D between the exciting coil and the detecting coil to the distance where the two signals are in opposite phases to each other and hence, to achieve the improved S/N ratio.

In addition, when the distance D between the exciting coil and the detecting coil is in the range of 4 mm to 10 mm, the two signals thereof have different phases. That is, the detection signal outputted from the detecting coil 10a, the detecting coil 10b in conjunction with the excitation of the exciting coil 11a, the exciting coil 11b by applying thereto the AC power, and the detection signal outputted from the detecting coil 10a, the detecting coil 10b in conjunction with the excitation of the detecting coil 10a, the detection coil 10b by applying thereto the AC power have different phases. When the two detection signals are synthesized, the noises induced by eccentricity or vibrations can be reduced. Even when the two detection signals are not in opposite phases to each other, the noises induced by eccentricity or vibrations can be reduced so that the S/N ratio is improved. In order to ensure the removal of the eccentricity-induced or vibration-induced noises, it is preferred to set the distance D between the exciting coil and the detecting coil to that the distance where the two detection signals are in opposite phases to each other. For the reduction of the noises induced by eccentricity or vibrations, however, it is only necessary to vary the phases of the two detection signals. Hence, the distance D between the exciting coil and the detecting coil need to be set depending upon the requirement of S/N ratio.

In the above-described specific examples, the difference between the inside diameter of the coil and the outside diameter of the specimen 3 inserted in the coil is 4 mm. The difference between the outside diameter of the specimen and the inside diameter of the coil is not limited to this. It is confirmed that there is the distance D between the exciting coil and the detecting coil where the two detection signals are in opposite phases to each other when the coil and the specimen have a variety of sizes. That is, the distance D between the exciting coil and the detecting coil has an optimum value depending upon a distance between the surface of the specimen and the coil.

According to the above-described first embodiment, the distance D between the exciting coil and the detecting coil is set such that the two detection signals are in opposite phases to each other in order to ensure the removal of the eccentricity-induced or vibration-induced noises.

Figure 8:
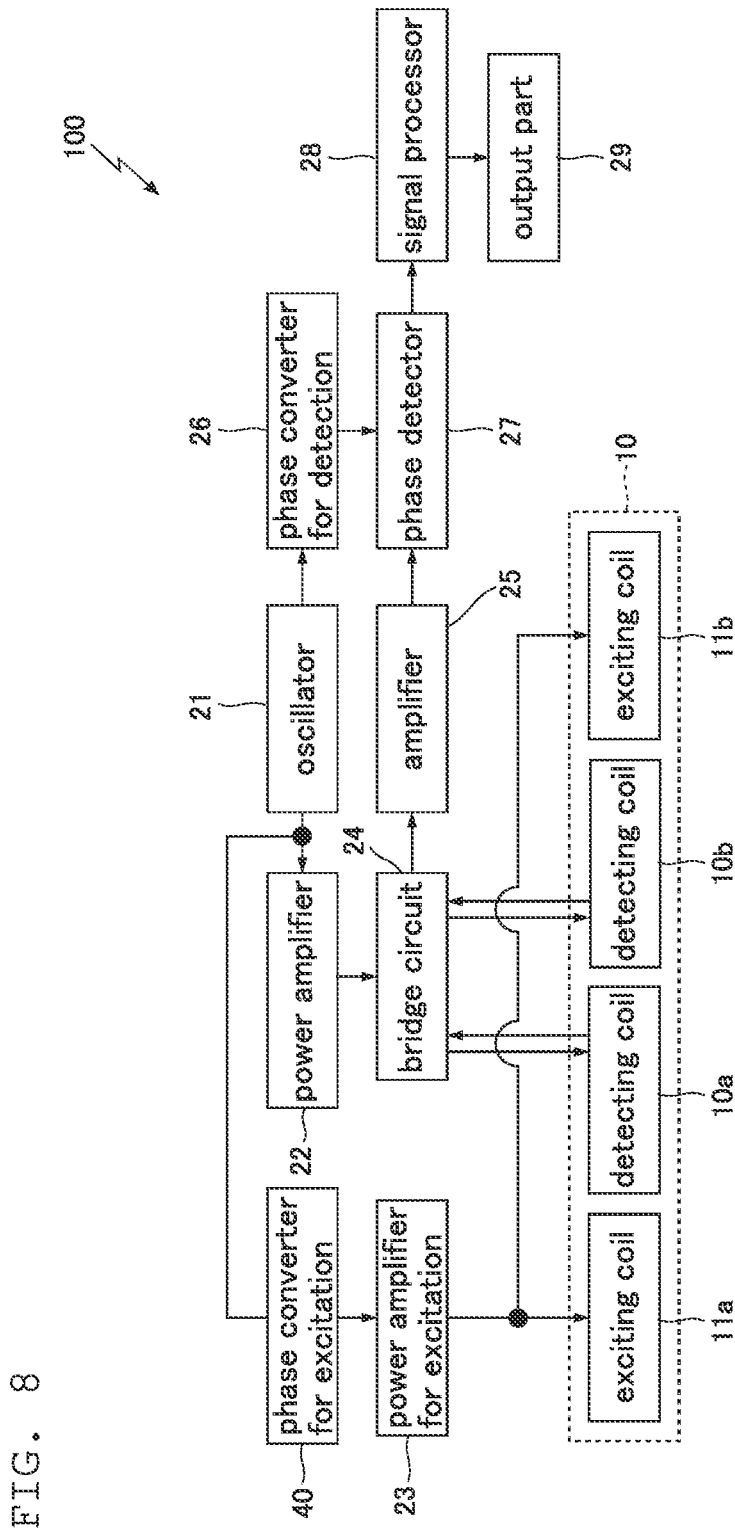
FIG. 8 is a block diagram showing an eddy current flaw detection apparatus according to a second embodiment of the invention.

According to a second embodiment shown in FIG. 8, the distance D between the exciting coil and the detecting coil is set to a predetermined value. In a case where the two detection signals are not in opposite phases to each other depending upon a difference between the inside diameter of the coil 10a, 10b, 11a, 11b and the outside diameter of the specimen 3, adjustment is made such that the phase of the signal applied to the exciting coil is converted so that the two signals are in opposite phases to each other. According to the second embodiment shown in FIG. 8, therefore, an AC output from the oscillator 21 is applied to a phase converter for excitation 40. It is noted that the second embodiment shown in FIG. 8 is configured the same way as the first embodiment except for that the phase converter for excitation 40 is provided. Therefore, identical (or equivalent) elements in the drawing are referred to by like reference numerals, the description of which is dispensed with.

As shown in FIG. 8, the AC output from the oscillator 21 is applied to the phase converter for excitation 40. The phase converter for excitation 40 converts the phase of the AC power for excitation to be applied to the exciting coils 11a, 11b. This phase converter 40 converts the phase of the AC power to be applied to the exciting coils 11a, 11b such that the two detection signals are in opposite phases to each other.

The AC power phase-converted by the phase converter for excitation 40 is applied to the power amplifier for excitation 23, which amplifies the AC power before applying the AC power to the exciting coils 11a, 11b.

Accordingly, the detection signal outputted from the detecting coil 10a, the detecting coil 10b in conjunction with the excitation of the exciting coil 11a, the exciting coil 11b by applying thereto the AC power phase-converted by the phase converter for excitation 40, and the detection signal outputted from the detecting coil 10a, the detecting coil 10b in conjunction with the excitation of the detecting coil 10a, the detection coil 10b by applying thereto the AC power are in opposite phases to each other. Thus, the apparatus can achieve the improved S/N ratio.

The above-described embodiments illustrate a case where encircling coils are used. However, the present invention is not limited to encircling coils but is also applicable to the use of inner coils and surface coils, and still the same effects are provided.

REFERENCE SIGNS LIST

3: specimen
10: probe
10a: detecting coil
10b: detecting coil
11a: exciting coil
11b: exciting coil
100: eddy current flaw detection apparatus
21: oscillator
22: power amplifier
23: power amplifier for excitation
24: bridge circuit
25: amplifier
26: phase converter for detection
27: phase detector
28: signal processor
29: output part
30: AC power source
40: phase converter for excitation
D: distance

What is claimed is:

1. An eddy current flaw detection apparatus comprising:
a pair of detecting coils arranged in contactless and coaxially spaced relation with a specimen; and
a bridge circuit two sides of which are constituted by the detecting coils so that magnetic fields generated by these detecting coils are in opposite phases to each other, wherein
a pair of exciting coils are arranged in a coaxial relation with and outside the detecting coils in a manner to sandwich the detecting coils therebetween, and the pair of detection coils and the pair of exciting coils are positioned with spaces between each of the air of detection coils and the pair of exciting coils along a direction in which the specimen extends, and
a distance between the detecting coil and the exciting coil adjacent thereto is set to a distance where a phase between an eccentricity-induced or vibration-induced noise signal which is excited in the exciting coil and detected by its adjacent detecting coil, and an eccentricity-induced or vibration-induced noise signal which is excited in the detecting coil and detected by the detecting coil changes.

2. The eddy current flaw detection apparatus according to claim 1, wherein the distance between the detecting coil and the exciting coil adjacent thereto is set to a distance where the eccentricity-induced or vibration-induced noise signal which is excited in the exciting coil and detected by its adjacent detecting coil, and the eccentricity-induced or vibration-induced noise signal which is excited in the detecting coil and detected by the detecting coil are in opposite phases to each other.

3. The eddy current flaw detection apparatus according to claim 1, wherein
a phase of an AC power applied to the exciting coil is converted such that the eccentricity-induced or vibration-induced noise signal which is excited in the exciting coil by the application of the AC power and detected by its adjacent detecting coil, and the eccentricity-induced or vibration-induced noise signal which is excited in the detecting coil by the application of the AC power and detected by the detecting coil are in opposite phases to each other.

4. The eddy current flaw detection apparatus according to claim 3, further comprising:
an oscillator;
a power amplifier for amplifying an AC output from the oscillator;
a phase converter for excitation which converts the phase of the AC output from the oscillator; and
a power amplifier for excitation which amplifies an AC output from the phase converter for excitation, wherein
the power amplifier applies the AC power to the detecting coil, and
the power amplifier for excitation applies the AC power to the exciting coil.

5. An eddy current flaw detection apparatus comprising:
a pair of detecting coils arranged in contactless and coaxially spaced relation with a specimen; and
a bridge circuit two sides of which are constituted by the detecting coils so that magnetic fields generated by these detecting coils are in opposite phases to each other, wherein
the specimen is a round bar,
a pair of exciting coils are arranged in a coaxial relation with and outside the detecting coils in a manner to sandwich the detecting coils therebetween,
the detecting coil and the exciting coil are encircling coils,
a distance between the detecting coil and the exciting coil adjacent thereto is set to a distance where a phase between an eccentricity-induced or vibration-induced noise signal which is excited in the exciting coil and detected by its adjacent detecting coil, and an eccentricity-induced or vibration-induced noise signal which is excited in the detecting coil and detected by the detecting coil changes, and
the distance between the detecting coil and the exciting coil adjacent thereto is set based on a difference between an outside diameter of the round bar and an inside diameter of the detecting coil and the exciting coil.

6. The eddy current flaw detection apparatus according to claim 5, wherein the distance between the detecting coil and the exciting coil adjacent thereto is set to a distance where the eccentricity-induced or vibration-induced noise signal which is excited in the exciting coil and detected by its adjacent detecting coil, and the eccentricity-induced or vibration-induced noise signal which is excited in the detecting coil and detected by the detecting coil are in opposite phases to each other.

7. The eddy current flaw detection apparatus according to claim 5, wherein
a phase of an AC power applied to the exciting coil is converted such that the eccentricity-induced or vibration-induced noise signal which is excited in the exciting coil by the application of the AC power and detected by its adjacent detecting coil, and the eccentricity-induced or vibration-induced noise signal which is excited in the detecting coil by the application of the AC power and detected by the detecting coil are in opposite phases to each other.

8. The eddy current flaw detection apparatus according to claim 7, further comprising:
- an oscillator;
- a power amplifier for amplifying an AC output from the oscillator;
  - a phase converter for excitation which converts the phase of the AC output from the oscillator; and
  - a power amplifier for excitation which amplifies an AC output from the phase converter for excitation, wherein
  - the power amplifier applies the AC power to the detecting coil, and
  - the power amplifier for excitation applies the AC power to the exciting coil.

9. The eddy current flaw detection apparatus according to claim 5, further comprising a probe disposed in proximity to the specimen, wherein
- the probe is formed in a cylindrical or semicylindrical shape and contains therein the detecting coils and the exciting coils.

10. The eddy current flaw detection apparatus according to claim 6, further comprising a probe disposed in proximity to the specimen, wherein
- the probe is formed in a cylindrical or semicylindrical shape and contains therein the detecting coils and the exciting coils.

11. The eddy current flaw detection apparatus according to claim 7, further comprising a probe disposed in proximity to the specimen, wherein
- the probe is formed in a cylindrical or semicylindrical shape and contains therein the detecting coils and the exciting coils.

12. The eddy current flaw detection apparatus according to claim 8, further comprising a probe disposed in proximity to the specimen, wherein
- the probe is formed in a cylindrical or semicylindrical shape and contains therein the detecting coils and the exciting coils.

* * * * *